US011872085B2

(12) United States Patent
Vortman et al.

(10) Patent No.: US 11,872,085 B2
(45) Date of Patent: Jan. 16, 2024

(54) FOCUSED ULTRASOUND SYSTEM WITH OPTIMIZED MONITORING OF CAVITATION

(71) Applicant: INSIGHTEC, LTD., Tirat Carmel (IL)

(72) Inventors: Kobi Vortman, Haifa (IL); Rafi De Picciotto, Tirat Carmel (IL)

(73) Assignee: INSIGHTEC, LTD., Tirat Carmel (IL)

( * ) Notice: Subject to any disclaimer, the term of this patent is extended or adjusted under 35 U.S.C. 154(b) by 144 days.

(21) Appl. No.: 17/057,920

(22) PCT Filed: Jun. 4, 2019

(86) PCT No.: PCT/IB2019/000644
§ 371 (c)(1),
(2) Date: Nov. 23, 2020

(87) PCT Pub. No.: WO2019/234497
PCT Pub. Date: Dec. 12, 2019

(65) Prior Publication Data
US 2021/0204915 A1   Jul. 8, 2021

Related U.S. Application Data

(60) Provisional application No. 62/681,282, filed on Jun. 6, 2018.

(51) Int. Cl.
*A61B 8/00* (2006.01)
*G01S 15/89* (2006.01)
*A61B 90/00* (2016.01)

(52) U.S. Cl.
CPC .............. *A61B 8/54* (2013.01); *A61B 8/4488* (2013.01); *G01S 15/8929* (2013.01); *A61B 2090/374* (2016.02); *A61B 2090/378* (2016.02)

(58) Field of Classification Search
CPC ... A61B 8/54; A61B 8/4488; A61B 2090/374; A61B 2090/378; A61B 5/055;
(Continued)

(56) References Cited

U.S. PATENT DOCUMENTS 11,291,866 B2 *   4/2022   Levy .................... G01S 7/5205
2007/0016039 A1   1/2007   Vortman et al.
(Continued)

FOREIGN PATENT DOCUMENTS

FR           3039994 A1     2/2017
JP        2005-500117 A     1/2005
(Continued)

OTHER PUBLICATIONS

International Search Report and Written Opinion corresponding to International Application No. PCT/IB2019/000644, dated Nov. 26, 2019, 14 pages.
(Continued)

*Primary Examiner* — Boniface Ngathi
*Assistant Examiner* — Zainab Mohammed Aldarraji
(74) *Attorney, Agent, or Firm* — Morgan, Lewis & Bockius LLP (57) ABSTRACT

Various approaches for generating an ultrasound focus at a target region and receiving signals therefrom using an ultrasound transducer having multiple transducer elements include acquiring multiple images of the target region and one or more path zones located on beam paths between the transducer elements and the target region; determining one or more tissue characteristics associated with the target region based on the acquired images; determining multiple profile parameters associated with each of the transducer elements based at least in part on the determined tissue characteristic; based at least in part on the profile parameters, operating at least first ones of the transducer elements to collectively transmit an ultrasound beam to the target region so as to create a focus thereon with desired properties; and based at least in part on the profile parameters, operating at least second ones of the transducer elements to receive acoustic signals from the target region and, in response (Continued)

thereto, adjusting operation of the at least first ones of the transducer elements to thereby improve the focus at the target region.

28 Claims, 8 Drawing Sheets

(58) Field of Classification Search
CPC ..... A61B 6/032; A61B 6/5211; A61B 8/0808; A61B 8/085; A61B 8/481; A61B 8/5215; A61B 2090/364; G01S 15/8929; G01S 7/52041; G01S 15/8927; A61N 7/02; A61N 2007/0039; A61N 2007/0078
See application file for complete search history.

(56) References Cited

U.S. PATENT DOCUMENTS

| | | | | |
|---|---|---|---|---|
| 2007/0167781 | A1* | 7/2007 | Vortman | ............. G10K 11/346 600/443 |
| 2010/0241036 | A1* | 9/2010 | Vortman | ................. A61N 7/02 601/3 |
| 2016/0008633 | A1* | 1/2016 | Vortman | ................. A61N 7/02 601/2 |
| 2016/0029969 | A1* | 2/2016 | Assif | .................... A61B 5/7217 600/411 |
| 2016/0157828 | A1* | 6/2016 | Sumi | ...................... G01N 29/46 702/189 |
| 2018/0326227 | A1 | 11/2018 | Sverdlik et al. | |
| 2019/0308038 | A1* | 10/2019 | Prus | ........................ A61N 7/02 |

FOREIGN PATENT DOCUMENTS

| | | | | |
|---|---|---|---|---|
| JP | 2014-117550 A | | 6/2014 | |
| WO | WO-2010082135 A1 | * | 7/2010 | ........... A61B 8/0816 |
| WO | WO2016/084081 A2 | | 6/2016 | |
| WO | WO-2016084081 A2 | * | 6/2016 | ............... A61N 7/00 |
| WO | WO-2017097853 A1 | * | 6/2017 | ....... A61B 17/22004 |
| WO | WO2018/020315 A1 | | 2/2018 | |
| WO | WO-2018020315 A1 | * | 2/2018 | ........... A61B 8/0808 |

OTHER PUBLICATIONS

Notice of Reasons for Refusal, JP2020-567768, dated Jun. 7, 2022, 9 pgs.

Second office action for corresponding Chinese Patent Application No. 201980038126.9 dated Jan. 11, 2023.

* cited by examiner

FIG. 5B

FOCUSED ULTRASOUND SYSTEM WITH OPTIMIZED MONITORING OF CAVITATION

CROSS-REFERENCE TO RELATED APPLICATION

This application is a U.S. National Phase Application of PCT/IB2019/000644, filed Jun. 4, 2019, which claims priority to and the benefits of U.S. Provisional Patent Application No. 62/681,282, which was filed on Jun. 6, 2018. The entire disclosures of these priority documents are hereby incorporated by reference in their entireties.

FIELD OF THE INVENTION

The present invention relates, generally, to a focused ultrasound system and, more particularly, to operating the focused ultrasound system to generate a high-quality focal zone and enable optimized monitoring of cavitation.

BACKGROUND

Focused ultrasound (i.e., acoustic waves having a frequency greater than about 20 kiloHertz) can be used to image or therapeutically treat a patient's internal body tissues. For example, ultrasound waves may be used in applications involving ablation of tumors, thereby eliminating the need for invasive surgery, targeted drug delivery, control of the blood-brain barrier, lysing of clots, and other surgical procedures. During an ultrasound procedure, a piezoceramic transducer is placed externally to the patient, but in close proximity to the tissue to be ablated or imaged (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases and amplitudes can each be controlled independently. Such a "phased-array" transducer facilitates steering the focal zone to different locations by adjusting the relative phases among the transducers; the focal volume may be shaped by controlling the amplitudes and phases associated with the elements. As used herein, the term "element" means either an individual transducer in an array or an independently drivable portion of a single transducer. Magnetic resonance imaging (MRI) may be used to visualize the patient and target, and thereby to guide the ultrasound beam.

As acoustic energy passes through tissue, it may interact with the tissue through multiple processes, including propagation, scattering, absorption, reflection, and refraction. The intensity of the acoustic energy reaching the target region and the size of the focal zone at the target region generally determine the therapeutic effectiveness of the treatment, i.e., the volume of tissue destroyed in the vicinity of the focal zone. The acoustic intensity and size of the focal zone depend upon system parameters such as transducer element characteristics, frequency of the acoustic energy, focal depth (the distance from the transducer to the focal zone), and power (amplitude), as well as patient-related parameters, such as tissue inhomogeneity.

For example, the size of the focal zone positively correlates to the square of the f-number of the ultrasound phased array—i.e., a smaller area of the focal zone corresponds to a lower f-number of the transducer elements. Because the f-number is defined as the ratio of the focal depth to the aperture width of the transducer elements, at a fixed focal distance, larger ultrasound emitting areas produce smaller focal-zone areas. Because a small focal zone corresponds a high acoustic intensity, it may be desirable to activate as many discrete transducer elements as possible in order to minimize the f-number.

On the other hand, it may also be beneficial to activate transducer elements to measure signals from the target region for the purposes of autofocusing and/or monitoring effects on the target resulting from the applied acoustic energy. This may be achieved utilizing small gas bubbles (or "microbubbles"). During a focused ultrasound treatment or ultrasound imaging session, microbubbles may be generated in the liquid fraction of the target tissue, e.g., due to the stress resulting from negative pressure produced by the propagating ultrasonic waves and/or due to rupture of the heated liquid and its accumulation as gas/vapor. Ultrasound signals reflected from the microbubbles may be utilized to establish a focus at the target region. In addition, depending upon the amplitude of the applied stress from an acoustic field, the microbubbles may collapse (this mechanism is called "inertial cavitation") and cause various thermal and/or mechanical effects in the target and/or its surrounding tissue. For example, at a low acoustic pressure, stable (streaming) cavitation of microbubbles may be induced to enhance energy absorption at the ultrasound focal region. Stable cavitation can allow tissue within the focal region to be heated faster and more efficiently than would occur in the absence of microbubbles. At a high acoustic pressure, however, unstable (or inertial) cavitation of the microbubbles may be induced, and this may cause undesired bio-effects such as hemorrhage, cell death, and extensive tissue damage beyond that targeted. Thus, it is important to monitor microbubble activity at the target and outside the target region so that the desired therapeutic bio-effects are obtained without damage to the non-target tissue.

Conventionally, acoustic signals from the microbubbles are detected using one or more hydrophones. The amount and quality of the detected signals depend on the total surface area of the hydrophones—a larger surface area combined by multiple hydrophones can detect more acoustic signals with higher signal-to-noise ratios (SNRs) compared to a smaller surface area of a single hydrophone. Therefore, conventional approaches typically require multiple hydrophones to be implemented in a solid angle around the target region for simultaneously detecting the acoustic signals therefrom.

Use of the hydrophones may be obviated by activating some elements in the transducer array to be used as hydrophones detecting signals from the microbubbles. But similar to arrangement utilizing hydrophones, it may also be necessary to activate as many transducer elements as hydrophones in the array as possible in order to receive sufficient signals with high SNRs in order to accurately determine the microbubble activity, localize the microbubble activity and/or perform ultrasound autofocusing. As a result, there is a trade-off between operating the transducer elements to emit waves to create a high-quality focus at the target and operating the transducer elements to receive signals from the microbubbles for autofocusing and/or detecting microbubble activity, and there is a need for an approach that facilitates selective optimization of this trade-off.

SUMMARY

The present invention provides systems and methods for optimally determining values of profile parameters (e.g., the mode of operation, amplitude, frequency, and/or phase) associated with each transducer element (or each group of transducer elements) as a function of time during the ultrasound procedure; the profile parameter values enable the transducer array to simultaneously create a focal zone having desired focusing properties at the target region and detect sufficient high-quality (e.g., high-SNR) signals from the microbubbles generated and/or introduced substantially close to the target region. The temporal profile parameter values may be determined based on, for example, imaging data of the target and/or non-target regions acquired prior to and/or during the ultrasound procedure. For example, for treatment of a brain tumor, the imaging data may define skull regions through which the ultrasound beams emitted from the transducer elements travel before reaching the target region; each skull region is associated with a transducer element. In various embodiments, based on anatomical characteristics (e.g., the structure, thickness or density) of the skull regions, their associated transducer elements are operated in a transmitting mode (so as to collectively generate a focal zone at the target region) or a receiving mode (so as to receive signals from the target region). For example, the transducer elements corresponding to thin skull regions may be operated in the transmitting mode to reduce beam aberrations and skull heating and the remaining elements may be operated in the receiving mode.

In some embodiments, a physical model involving a thermo-acoustic simulation is utilized to predict acoustic paths of ultrasound beams from the transducer elements to the target region and estimate "heating profiles"—that is, the expected change in tissue temperature for a given level of applied acoustic energy—of the skull regions based on their anatomical characteristics (e.g., bone density). Operation of each transducer element (i.e., in the transmitting or receiving mode) can be determined based on the model prediction. For example, the transducer elements corresponding to skull regions that have high heating profiles may be operated in the receiving mode in order to avoid overheating of the skull.

In various embodiments, the profile parameters of the transducer elements may be determined based on acoustic signals from the target region measured prior to and/or during the ultrasound procedure. In addition, each transducer element may alternate between the transmitting and receiving mode during the procedure. The optimal temporal pattern of mode changes may be determined for each element based on, for example, the imaging data, thermoacoustic simulation results and/or acoustic signals from the target/non-target regions.

In some embodiments, the transducer elements are substantially simultaneously operated in both transmitting and receiving modes. A spectral filter may then be employed to filter signals having the transmission frequency in order to permit analysis of the reflections; this may advantageously avoid amplitude saturation of the transducer receiving circuits resulting from the large transmitted signals. In addition, the frequency range of the signals detected by each transducer element may be selected (e.g., using a filter) for providing more sensitive measurements to a specific microbubble cavitation event.

Finally, the ultrasound transmission frequency may be optimized based on the anatomical characteristics of the target and/or non-target tissues for maximizing the acoustic intensity at the target region. The transducer elements may be driven with the optimized frequency.

Accordingly, the present invention provides various approaches for driving the ultrasound transducer elements so as to generate a high-quality focal zone at the target region and enable measurements of high-quality signals from the target region.

Accordingly, in one aspect, the invention pertains to a system for generating an ultrasound focus at a target region and receiving signals therefrom. In various embodiments, the system includes an ultrasound transducer having multiple transducer elements; an imaging system for obtaining multiple images of (i) the target region and (ii) one or more path zones located on beam paths between at least some of the transducer elements and the target region; and a controller, operably coupled to the ultrasound transducer and the imaging system. In one implementation, the controller is configured to (a) determine one or more tissue characteristics (e.g., the tissue type, location, size, thickness, density, structure, shape, vascularization, thermal time constant, etc.) associated with the target region based on the obtained images; (b) determine multiple profile parameters (e.g., a mode of operation, an amplitude, a frequency and/or a phase) associated with each of the transducer elements based at least in part on the determined tissue characteristic(s); (c) based at least in part on the profile parameters, operate the first ones of the transducer elements to collectively transmit an ultrasound beam to the target region so as to create a focus thereon; and (d) based at least in part on the profile parameters, operate the second ones of the transducer elements to receive acoustic signals from the target region and, in response thereto, adjust operation of the first ones of the transducer elements to thereby improve the focus at the target region.

The system may further include an administration device for introducing microbubbles into the target region. Additionally or alternatively, the administration device may introduce a seed microbubble; the controller is then further configured to cause generation of a cloud of microbubbles at the target region using the seed microbubble and the ultrasound transducer. In one embodiment, the controller is further configured to cause generation of microbubbles in the target region using the ultrasound transducer. The received signals are reflections from the generated/introduced microbubbles. In addition, the controller may be further configured to detect a cavitation characteristic (e.g., a cavitation type and/or a cavitation location) of the microbubbles based at least in part on the received signals. In one embodiment, the controller is further configured to determine the profile parameters based at least in part on the received signals; and operate the first and second ones of the transducer elements based on the profile parameters.

In various embodiments, the imaging system is configured to obtain the second set of images of (i) the first tissue region surrounding the target region and/or (ii) the second tissue region on one of the path zones; the controller is further configured to determine one or more second tissue characteristics (e.g., the tissue type, location, size, thickness, density, structure, shape, vascularization, thermal time constant, etc.) associated with the first tissue region and/or the second tissue region based on the obtained second set of images. In addition, the controller may be further configured to determine the profile parameters based at least in part on the second tissue characteristic(s); and adjust operation of the transducer elements based on the determined profile parameters. In some embodiments, the controller is further configured to predict acoustic paths of ultrasound beams transmitted from the first ones of the transducer elements; and estimate heating profiles of the first and second regions based at least in part on the second tissue characteristic(s). In one implementation, the acoustic path prediction and heating profile estimation is performed using a physical model including a thermo-acoustic simulation.

In one embodiment, at least some of the first ones of the transducer elements are different from at least some of the second ones of the transducer elements. In another embodiment, at least some of the first ones of the transducer elements are the same as at least some of the second ones of the transducer elements. In addition, the controller may be further configured to substantially simultaneously operate the first ones of the transducer elements that are the same as the second ones of the transducer elements. In one implementation, the system further includes a spectral filter for filtering the received signals having a frequency of the transmitted ultrasound beam. In addition, the system may include a time-division multiplexer; the first ones of the transducer elements and the second ones of the transducer elements are operated during different time slices. The first time interval of the time slices associated with operation of the first ones of the transducer elements may be the same as or different from the second time interval of the time slices associated with operation of the second ones of the transducer elements.

In various embodiments, the controller is further configured to determine a frequency range of the received acoustic signals. The system may further include a spectral filter for filtering the received signals having frequencies outside the frequency range. In addition, the controller may be further configured to determine the frequency range based on the second tissue characteristic(s) (e.g., the tissue type, location, size, thickness, density, structure, shape, vascularization, thermal time constant, etc.) associated with an intervening tissue located in at least one of the path zones. In one embodiment, the controller is further configured to determine an optimal transmission frequency associated with the first ones of the transducer elements for maximizing an acoustic intensity at the target region. For example, the controller may be further configured to determine the optimal transmission frequency based at least in part on the tissue characteristic(s) of the target region and the second tissue characteristic(s) associated with an intervening tissue located in one or more of the path zones.

In another aspect, the invention relates to a method for generating an ultrasound focus at a target region and receiving signals therefrom using an ultrasound transducer having multiple transducer elements. In various embodiments, the method includes acquiring multiple images of the target region and one or more path zones located on beam paths between the transducer elements and the target region; determining one or more tissue characteristics (e.g., the tissue type, location, size, thickness, density, structure, shape, vascularization, thermal time constant, etc.) associated with the target region based on the acquired images; determining multiple profile parameters (e.g., a mode of operation, an amplitude, a frequency and/or a phase) associated with each of the transducer elements based at least in part on the determined tissue characteristic(s); based at least in part on the profile parameters, operating the first ones of the transducer elements to collectively transmit an ultrasound beam to the target region so as to create a focus thereon; and based at least in part on the profile parameters, operating the second ones of the transducer elements to receive acoustic signals from the target region and, in response thereto, adjusting operation of the first ones of the transducer elements to thereby improve the focus at the target region.

The method may further include introducing microbubbles into the target region. Additionally or alternatively, the method may further include causing generation of microbubbles in the target region using the ultrasound transducer. In one embodiment, the method further includes introducing a seed microbubble and causing generation of a cloud of microbubbles at the target region using the seed microbubble and the ultrasound transducer. The received signals are reflections from the generated/introduced microbubbles. In addition, the method may further include detecting a cavitation characteristic (e.g., a cavitation type and/or a cavitation location) of the microbubbles based at least in part on the received signals. In one embodiment, the method further includes determining the profile parameters based at least in part on the received signals; and operating the first and second ones of the transducer elements based on the profile parameters.

In various embodiments, the method further includes obtaining the second set of images of the first tissue region surrounding the target region and/or the second tissue region on one of the path zones; and determining one or more second tissue characteristics (e.g., the tissue type, location, size, thickness, density, structure, shape, vascularization, thermal time constant, etc.) associated with the first tissue region and/or the second tissue region based on the obtained second set of images. In addition, the method may further include determining the profile parameters based at least in part on the second tissue characteristic(s); and adjusting operation of the transducer elements based on the determined profile parameters. In some embodiments, the method further includes predicting acoustic paths of ultrasound beams transmitted from the first ones of the transducer elements; and estimating heating profiles of the first and second regions based at least in part on the second tissue characteristic(s). In one implementation, the acoustic path prediction and heating profile estimation is performed using a physical model including a thermo-acoustic simulation.

In one embodiment, at least some of the first ones of the transducer elements are different from at least some of the second ones of the transducer elements. In another embodiment, at least some of the first ones of the transducer elements are the same as at least some of the second ones of the transducer elements. In addition, the method may further include substantially simultaneously operating the first ones of the transducer elements that are the same as the second ones of the transducer elements. In one implementation, the method further includes applying a spectral filter to filter the received signals having a frequency of the transmitted ultrasound beam. In addition, the method may further include operating the first ones of the transducer elements and the second ones of the transducer elements during different time slices. The first time interval of the time slices associated with operation of the first ones of the transducer elements may be the same as or different from the second time interval of the time slices associated with operation of the second ones of the transducer elements.

In various embodiments, the method further includes determining a frequency range of the received acoustic signals. The method may further include applying a spectral filter to filter the received signals having frequencies outside the frequency range. In addition, the method may further include determining the frequency range based on the second tissue characteristic(s) (e.g., the tissue type, location, size, thickness, density, structure, shape, vascularization, thermal time constant, etc.) associated with an intervening tissue located in at least one of the path zones. In one embodiment, the method further includes determining an optimal transmission frequency associated with the first ones of the transducer elements for maximizing an acoustic intensity at the target region. For example, the method may further include determining the optimal transmission frequency based at least in part on the tissue characteristic(s) of the target region and the second tissue characteristic(s) associated with an intervening tissue located in one or more of the path zones.

As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
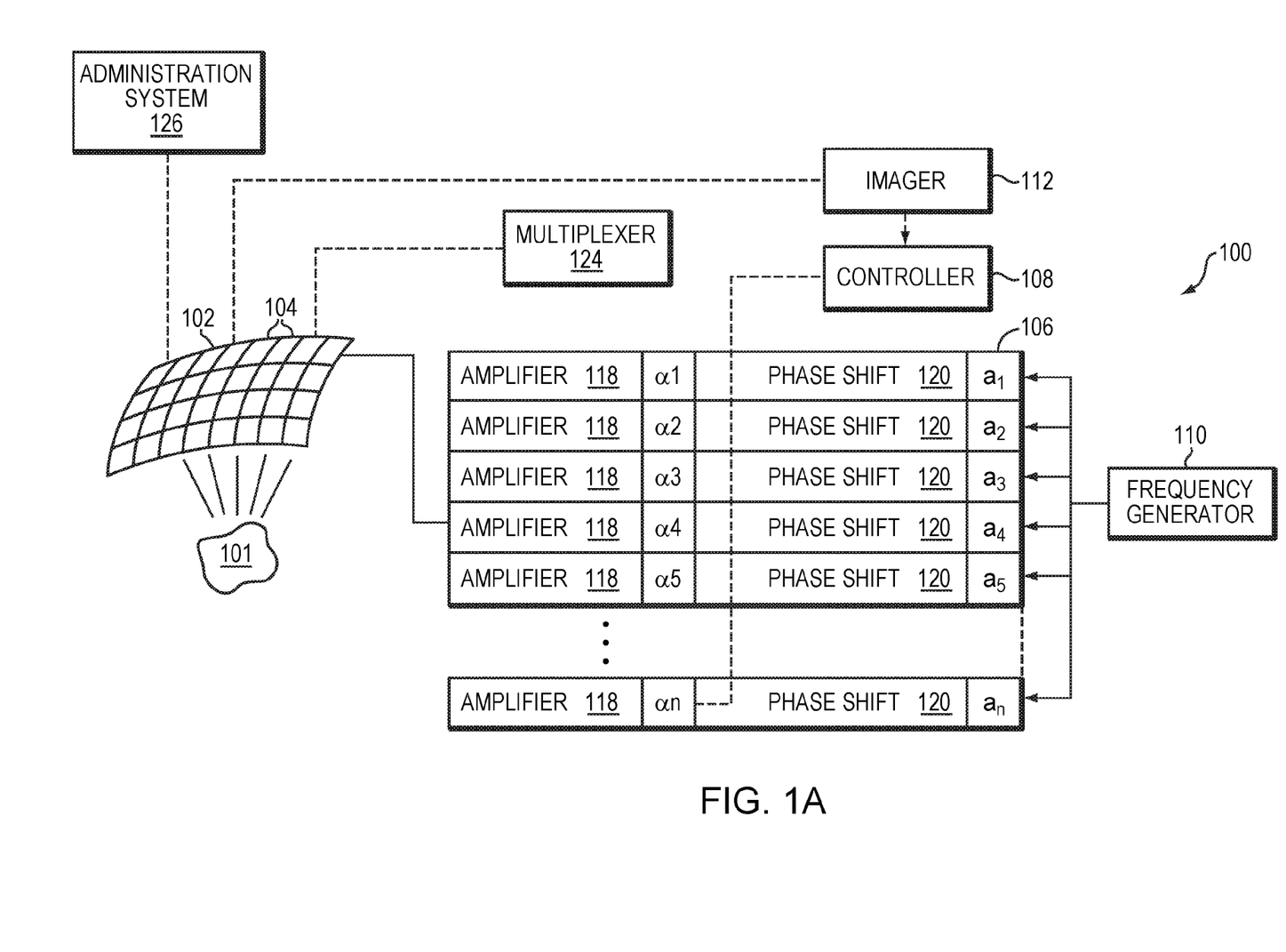
FIG. 1A schematically depicts an exemplary ultrasound system in accordance with various embodiments of the current invention.

FIG. 1A illustrates an exemplary ultrasound system 100 for focusing ultrasound onto a target region 101 in a patient. The system 100 can shape the ultrasonic energy in various ways, producing, for example, a point focus, a line focus, a ring-shaped focus, or multiple foci simultaneously. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of a skull or a body part other than the skull, or may include one or more planar or otherwise shaped sections. Its dimensions may vary, depending on the application, between millimeters and tens of centimeters. The transducer elements 104 of the array 102 may be piezoelectric ceramic, capacitive micromachined ultrasonic transducer (CMUT) or microelectromechanical systems (MEMS) elements, and may be mounted in silicone rubber or any other material suitable for damping the mechanical coupling between the elements 104. Piezo-composite materials, or generally any materials shaped in such a way that is capable of converting electrical energy to acoustic energy, may also be used. To assure maximum power transfer to the transducer elements 104, the elements 104 may be configured for electrical resonance, matching input impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase shift circuit 120; drive circuit drives one of the transducer elements 104. The beamformer 106 receives a radio frequency (RF) input signal, typically in the range from 0.1 MHz to 4.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull or different tissues located in the acoustic paths of ultrasound beams from the transducer elements to the target region or "path zones") onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of intervening tissues located between the transducer 102 and the target 101 and their effects on propagation of acoustic energy. In various embodiments, such information is obtained from an imager 112, such as a magnetic resonance imaging (MRI) device, a computer tomography (CT) device, a positron emission tomography (PET) device, a single-photon emission computed tomography (SPECT) device, or an ultrasonography device. The imager 112 may provide a set of two-dimensional images suitable for reconstructing a three-dimensional image of the intervening tissues from which thicknesses and densities can be inferred; alternatively, image acquisition may be three-dimensional.

In some embodiments, the ultrasound system 100 may include a multiplexer 124 coupled to the beamformer 106 for controlling the drive signals associated with the transducer elements 104. As further described below, the transducer array 102 may then be configured to substantially simultaneously transmit beams to and receive signals from the target 101. In addition, image-manipulation functionality may be implemented in the imager 112, in the controller 108, or in a separate device. In some embodiments, the ultrasound system 100 may include an administration system 126 for parenterally introducing the microbubbles 202 into the patient's body. The microbubbles 202 may be introduced in the form of liquid droplets that subsequently vaporize, as gas-filled bubbles, or entrained with another suitable substance, such as a conventional ultrasound contrast agent. The administration system 126 may be any suitable apparatus for delivering a suspension of microbubbles into the patient's bloodstream, and can take the form of, e.g., a manual or automated syringe, an intravenous administration bag and needle set, a peristaltic pump, etc.

Figure 1B:
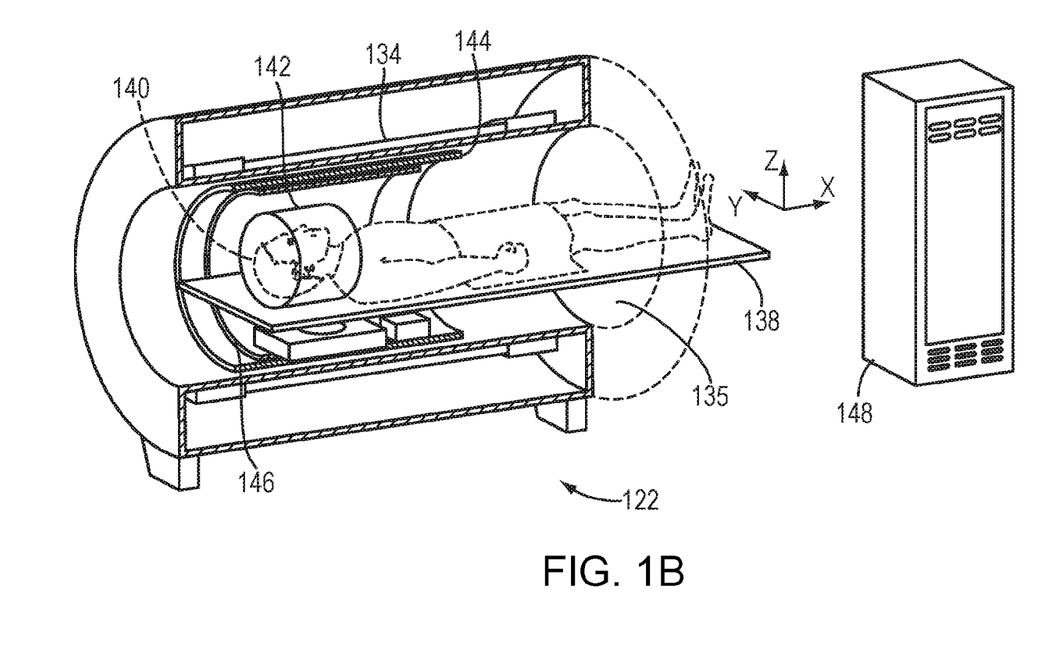
FIG. 1B schematically depicts an exemplary MRI system in accordance with various embodiments of the current invention.

FIG. 1B illustrates an exemplary imager—namely, an MRI apparatus 112. The apparatus 112 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 112 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region (e.g., a tumor or a target BBB) can be identified.

To perform targeted drug delivery or tumor ablation, it is necessary to determine the location of the target region 101 with high precision. Accordingly, in various embodiments, the imager 112 is first activated to acquire images of the target region 101 and/or non-target region (e.g., the healthy tissue surrounding the target region, the intervening tissue located between the transducer array 102 and the target region 101 and/or any regions located near the target) and, based thereon, determine anatomical characteristics (e.g., the tissue type, location, size, thickness, density, structure, shape, vascularization) associated therewith. For example, a tissue volume may be represented as a 3D set of voxels based on a 3D image or a series of 2D image slices and may include the target region 101 and/or non-target region.

Figure 2:
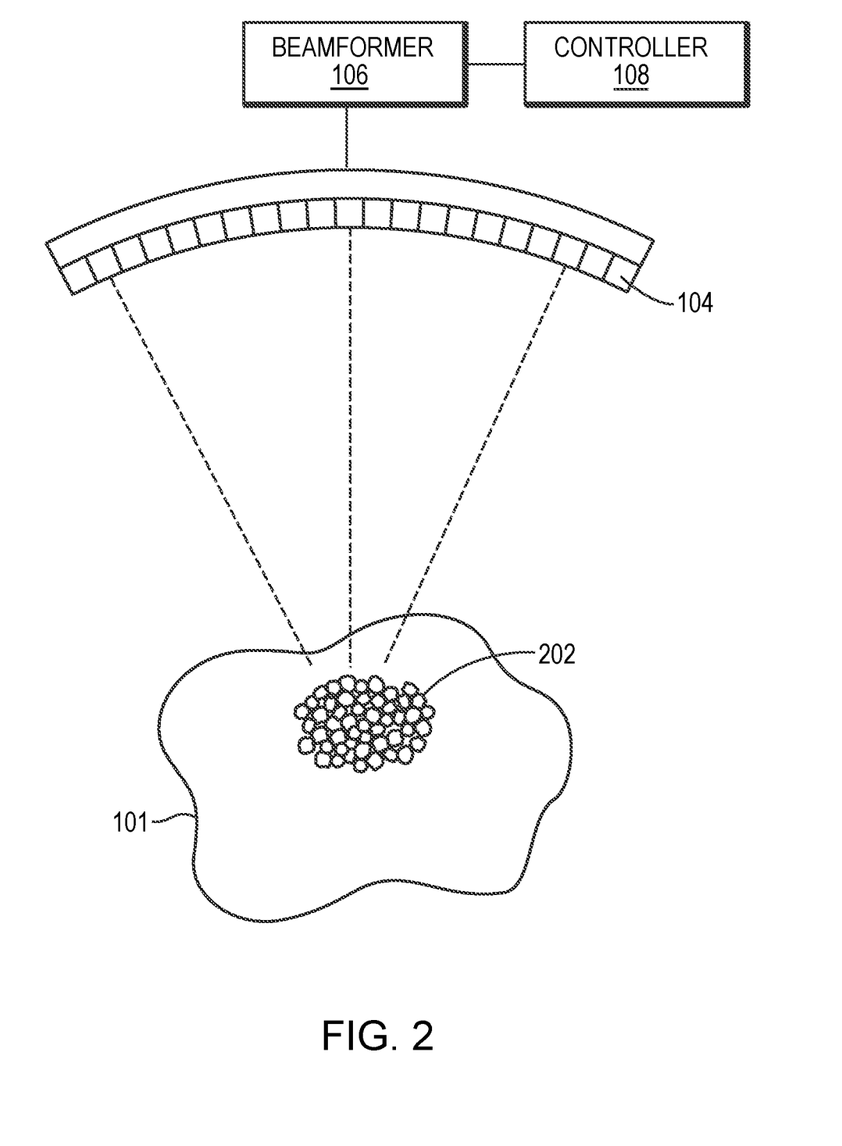
FIG. 2 depicts generation and/or introduction of microbubbles into a target region for autofocusing in accordance with various embodiments.

Referring to FIG. 2, in various embodiments, the acoustic energy emitted by the transducer elements 104 may be above a threshold and thereby cause generation of microbubbles 202 in the liquid contained in the tissue. The microbubbles can be formed due to the negative pressure produced by the propagating ultrasonic waves or pulses, or when the acoustically heated liquid ruptures and is filled with gas/vapor, or when a mild acoustic field is applied to tissue that already contains cavitation nuclei. Because of their encapsulation of gas, the microbubbles 202 reflect ultrasound and the reflections therefrom can provide information about the focusing properties at the target region 204. Additionally or alternatively, the microbubbles 202 may be introduced parenterally by the administration system 126. In some embodiments, the administration device 126 introduces a seed microbubble into the target region 101; the transducer 102 is then activated to transmit ultrasound waves to the seed microbubble for generating a cloud of microbubbles 202 (nucleation). Approaches to generating the microbubbles and/or introducing the microbubbles to the target region 101 are provided, for example, in PCT Publication No. WO 2018/020315, PCT Application Nos. PCT/US2018/064058 (filed on Dec. 5, 2018), PCT/IB2018/001103 (filed on Aug. 14, 2018), PCT/US2018/064892 (filed on Dec. 11, 2018), PCT/IB2018/000841 (filed on Jun. 29, 2018), and PCT/US2018/064066 (filed on Dec. 5, 2018), U.S. Patent Publication No. 2019/0083065, and U.S. patent application Ser. No. 15/837,392 (filed on Dec. 11, 2017), the contents of which are incorporated herein by reference. In some embodiments, ultrasound reflections/emissions from the microbubbles 202 are measured using the transducer elements 104 and/or other detector devices (e.g., hydrophones), which then transmit the resulting signals to the controller 108. The measured signals may be analyzed in order to facilitate automatic focus of the ultrasound beams at the target region and/or to monitor microbubble cavitation events as further described below. Approaches to autofocusing and monitoring microbubble cavitation events using signals from the microbubbles are described, for example, in PCT Publication No. WO 2018/020315, U.S. Patent Publication No. 2018/0206816, and the International Application entitled "Improved Reflection Autofocusing" filed on even date herewith, the contents of which are incorporated herein by reference.

In various embodiments, each individual transducer element 104 can be operated in two modes—a transmitting mode and a receiving mode; the transmitting mode delivers acoustic energy to the target region 101, and the receiving mode detects acoustic signals from the microbubbles 202 at the target. In addition, the transducer elements may be deactivated (deactivation mode) if desired. Further, the transducer elements may be used in the transmitting mode followed by the receiving mode in a temporally separated manner.

In some embodiments, the transducer elements 104 are grouped, and elements within each group are operated together so as to receive a drive signal from a single channel. Each group may comprise a one, two or three dimensional array (i.e., a row, a matrix or a curved matrix) of transducer elements 104; different groups may or may not share one or more transducer elements 104. The elements within each group may form a single contiguous area of the transducer surface, or may include multiple non-contiguous surface portions. In various embodiments, the groups of transducer elements 104 are separately controllable. For example, they may each be capable of emitting ultrasound waves with frequencies, amplitudes and/or phases that are independent of the frequencies, amplitudes and/or phases of the other groups. In addition, each group can be operated in the transmitting or receiving mode or deactivated, independent of the mode of operation other groups.

Operation of the transducer elements 104 (or groups of the elements 104) may be specified by their profile parameters (such as the mode of operation, amplitude, frequency, and/or phase associated with each transducer element or each group of transducer elements) as a function of time. In various embodiments, these temporal profile parameters are determined to achieve optimal focusing properties at the target region 101 and simultaneously obtain high-quality (e.g., high-SNR) signals from the microbubbles 202 for the purposes of autofocusing and/or monitoring the microbubble activity. The controller 108 may control operation of the transducer elements 104 (e.g., switching between transmitting and receiving modes) based on the determined profile parameters.

In various embodiments, the profile parameters are determined based on imaging data of the target and/or non-target regions (including the tissue surrounding the target region and intervening tissue located between the target and the transducer elements 104) acquired using the imager 112 prior to and/or during the ultrasound procedure. By analyzing the imaging data, tissue information—such as the types, locations and anatomical characteristics (e.g., the thickness, density and geometry) of the target tissue and non-target tissue—can be obtained. In addition, based on the acquired tissue information and/or clinical requirements (e.g., a maximum tolerable temperature) associated therewith, the operating mode of each transducer element (or each group of transducer elements) can be optimally determined. For example, referring to FIG. 3A, to efficiently transmit acoustic energy to a brain tumor 302 through the patient's skull and receive sufficient high-quality signals from the microbubbles at the tumor 302, the operating modes of the transducer elements 104 may be determined based on the thickness of the skull. In one embodiment, thin skull regions (e.g., temples) 304 on the beam paths from the transducer elements 306 to the tumor 302 are first identified using the imaging data. Because these thin skull regions 304 may cause less aberration of the ultrasound beams compared to other, thicker skull regions 308, all of the transducer elements 306 associated with (i.e., whose beams will pass through) the thin skull regions 304 may be activated in the transmitting mode for efficiently delivering energy to the tumor 302. All (or at least some) other transducer elements 310 may be activated in the receiving mode to detect acoustic signals from the microbubbles.

Figure 3A:
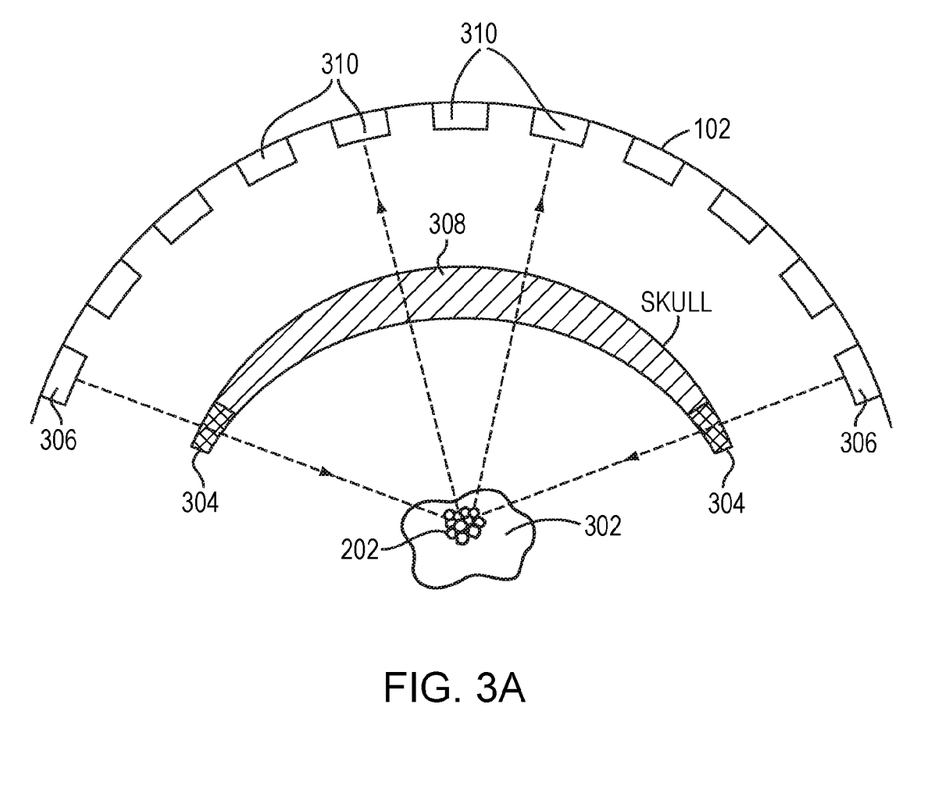
FIG. 3A depicts operations of the transducer elements based at least in part on the anatomical characteristics of intervening tissue located along the acoustic paths of ultrasound beams from the transducer elements to the target region in accordance with various embodiments.
Figure 3B:
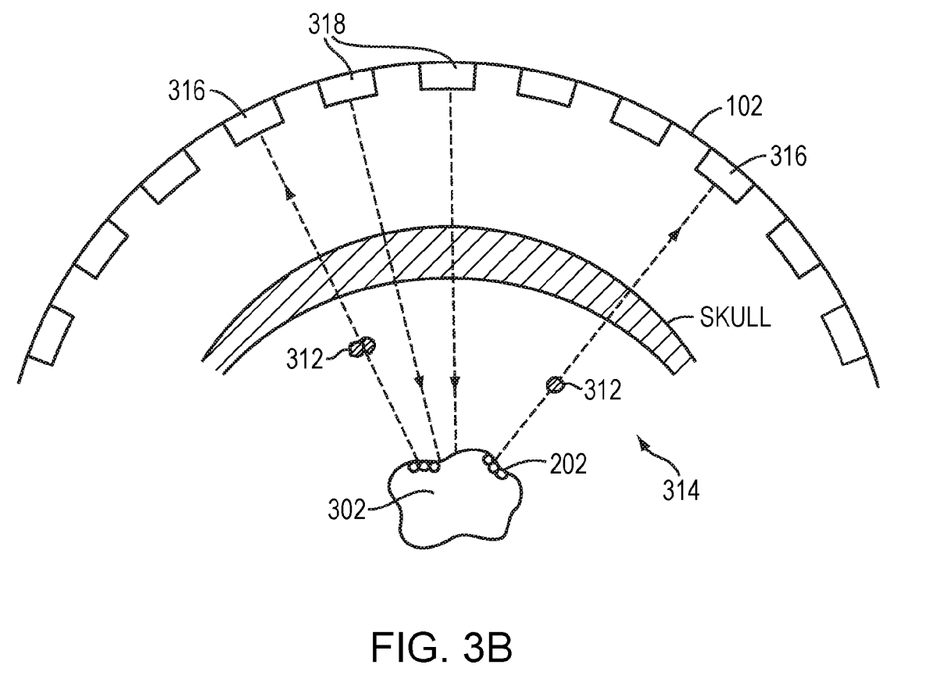
FIG. 3B depicts operations of the transducer elements based at least in part on the locations of calcifications in accordance with various embodiments.

With reference to FIG. 3B, in some embodiments, calcifications 312 in the intervening tissue (e.g., brain) 314 can be identified using the imaging data. Because calcifications 312 may result in an undesired temperature increase in the tissue neighboring the calcifications when traversed by the ultrasound beams (due to its high acoustic absorption), it may be advantageous to avoid (or at least reduce) ultrasound transmission therethrough. Accordingly, in one embodiment, based on the identified locations of the calcifications 312 and the target 302 and the transducer geometry, a physical model that predicts beam paths traveling though the intervening tissue may be employed to identify the transducer elements 316 whose emitted beams will likely traverse the calcification sites 312 prior to reaching the target 302. These elements 316 may then be activated in the receiving mode to measure acoustic signals from microbubbles in the target/non-target regions. The remaining elements 318 (or at least some of them) whose beam paths do not traverse the calcification sites 312 may be activated in the transmitting mode to deliver acoustic energy to the target region. In one embodiment, the information about calcifications can be combined with the skull characteristics to determine the mode of operation of the transducer elements.

Operation of the transducer elements may be continuous—i.e., the transducer elements 306, 318 may continuously transmit waves to the target region 302 and the transducer elements 310, 316 may continuously receive signals from the target region 302 through the entire ultrasound procedure. Alternatively, the transducer elements may be operated based on a temporal pattern. In one embodiment, the temporal pattern is determined based on tissue characteristics acquired using the imaging data. For example, transmission from the transducer elements 306 may be temporarily halted in a periodic manner (e.g., 1 msec for every 10 msec) to avoid overheating of the skull. Similarly, signals from the target 302 may be periodically measured (e.g., every 3 minutes) by the transducer elements 310 to minimize undesired heating. In addition, the temporal operation pattern of the transducer elements may be determined based on acoustic signals from the microbubbles 202 measured prior to and/or during the ultrasound procedure as further described below.

In some embodiments, the physical model includes a thermo-acoustic simulation involving multiple steps. First, the simulation may predict the acoustic path from each relevant transducer element to the target through a skull region using, e.g., information acquired by the imaging data and transducer geometry as described above. In addition, the simulation may perform thermal simulations to estimate how different skull regions absorb the acoustic energy and have different heating profiles based on their anatomical characteristics acquired by the imaging data and/or acoustic beam frequency. The simulation may then identify the skull regions that will likely absorb significant amounts of energy to cause the temperature thereof to rise above a predetermined threshold value. In some embodiments, the transducer elements associated with these identified skull regions are operated in the receiving mode to avoid overheating of the skull, and the remaining elements (or at least some of them) corresponding to the skull regions having low heating profiles are operated in the transmitting mode.

Additionally or alternatively, the profile parameters of the transducer elements may be determined based on acoustic signals from the target region measured immediately before and/or during the ultrasound procedure. For example, after the transducer elements are calibrated but prior to being activated for the ultrasound procedure, all (or at least some) transducer elements may be operated in the transmitting mode to emit signals to the target; the transducer elements may be subsequently switched to the receiving mode to detect signals reflected from the target. In one embodiment, the detected signals are analyzed by the controller 108 to determine their SNRs. The elements 104 that detect signals having SNRs above a predetermined threshold may then be operated in the receiving mode during the ultrasound procedure. Other elements corresponding to received signals having low SNRs may be operated in the transmitting mode.

Figure 4:
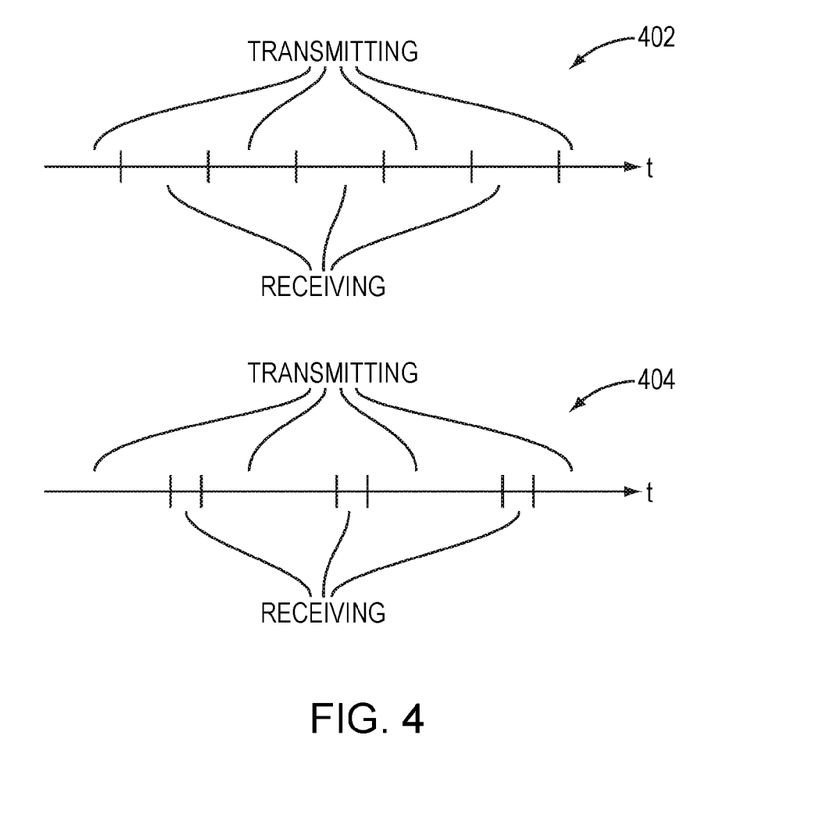
FIG. 4 depicts operations of the transducer elements in transmitting and receiving modes in accordance with various embodiments.

In addition, each individual transducer element 104 (or each group of transducer elements) may alternate between transmitting ultrasound signals to the microbubbles 202 and receiving ultrasound signals reflected from the microbubbles 202. For each element 104, the time interval of the transmitting mode may be the same or different from that of the receiving mode. In addition, different transducer elements 104 may have the same or different transmitting-mode and receiving-mode time intervals. For example, referring to FIG. 4, a transducer element 402 may be operated in transmitting and receiving modes having the same time intervals, while another transducer element 404 may be operated in the transmitting mode with a time interval that is longer than that of the receiving mode. Again, the time intervals of the transmitting and receiving modes associated with each transducer element 104 may be determined based on the imaging data (e.g., tissue information of the target/non-target regions), thermo-acoustic simulation results and/or acoustic signals from the target/non-target regions, and the position of the transducer element in the array.

In one embodiment, the transducer array 102 may be configured to substantially simultaneously transmit beams to and receive signals from the target 101. For example, referring again to FIG. 1, the ultrasound system 100 may include a multiplexer 124 coupled to the beamformer 106 for controlling the drive signals associated with the transducer elements 104. In time-division multiplexing (TDM), the drive signals of the transmitting mode and receiving mode associated with each transducer element are partitioned among timeslices; that is, the signals physically "take turns" on a divided time domain of the signal channel. In one implementation, the time intervals of the slices that cause the transducer elements to be operated in the receiving mode are determined based on the acoustic and/or thermal time constants of the targeted tissue. For example, the time intervals of driving the element 104 in the receiving mode may be smaller than the time constants of the target tissue; this ensures that the tissue responses are not significantly affected by operating the transducer elements in the receiving mode. Approaches for determining the time constants of the target tissue are provided, for example, in U.S. Patent Publication No. 2018/0360420, the contents of which are incorporated herein by reference.

When the transducer elements 104 are substantially simultaneously driven in the transmitting and receiving modes, the large transmitted signal may immediately saturate the sensitive receiving circuits. When the transmitted drive signal ends, it may take some time for a transmitting transducer's electrical output signal to decay to an amplitude small enough that it no longer saturates the receiving circuits; this may cause a delay in the signal measurements. Accordingly, in various embodiments, the receiving circuits include a spectral filter (which may be implemented in hardware and/or software if the dynamic range of the receiving channel is wide enough to avoid saturation in the preprocessing stage) to filter out the signals having the transmission frequency. As a result, saturation of the receiving circuits during the transmitting mode is avoided; this approach thus allows the transducer elements to be operated substantially simultaneously in the transmitting and receiving modes, while enabling detection of signals from the microbubbles without a significant delay.

Generally, various types of microbubble cavitation may occur during the ultrasound procedure and each type of the cavitation at each location may have its own spectral "signature" that represents the unique response of the bubbles. For example, stable cavitation induced at an intermediate acoustic power may produce a strong sub-harmonic response (i.e., having more components at the sub-harmonic frequencies and/or having larger amplitudes of the sub-harmonic frequencies); whereas inertial cavitation induced at a high acoustic power may produce broadband (white) noise. Accordingly, by detecting and analyzing the acoustic signals emitted from the microbubbles, the presence, type and/or location of cavitation induced in tissue during the ultrasound procedure can be determined. Approaches to determining the presence, type and/or location of microbubble cavitation using signals from the microbubbles are described, for example, in U.S. Patent Publication No. 2018/0206816, the content of which is incorporated herein by reference.

When the acoustic signals from the microbubbles travel from the microbubbles to the transducer elements, the inhomogeneity of different types of tissues (e.g., the skull and/or brain tissues) intervening between the microbubbles and the transducer elements 104 may change certain characteristics of the spectral signatures. In various embodiments, the physical model described above is implemented to predict the change in the acoustic signals resulting from the inhomogeneous intervening tissues based on, for example, the tissue information acquired from the imager data and/or the transducer geometry. In some embodiments, the change in the spectral signatures is quantified using a modulation-transfer function on an element-by-element basis. Accordingly, based on the signatures of microbubble cavitation events and the change in the spectral signals predicted using modulation-transfer functions, the detected frequency range of each transducer element in the receiving mode can be selected or adjusted (e.g., using filters) so as to allow more sensitive measurement of the signals from the microbubbles.

Generally, the goal of the ultrasound procedure is to maximize the amount of energy absorbed at the target region while minimizing the exposure of healthy non-target tissue to ultrasound. The degree of ultrasound absorption in tissue is a function of frequency, given by:

$$I = I_0 e^{-2\alpha f z}$$

where $I_0$ is the ultrasound intensity at the point of entry into the tissue (measured in W/cm$^2$), I is the intensity after beam propagation through the tissue over a distance z (which is measured in cm), f is the frequency of the ultrasound (measured in MHz), and $\alpha$ is the absorption coefficient at that frequency (measured in cm$^{-1}$·MHz$^{-1}$). Higher values of the product $\alpha \cdot f$ produce greater degrees of absorption in the target region but also larger fractions of ultrasound that are absorbed before reaching the target region. Therefore, at a certain depth, z, in tissue, the ultrasound frequency of the applied waves may reflect a trade-off between the absorption of the acoustic power in the path zone and the peak intensity at the focal zone. In some embodiments, the ultrasound transmission frequency is determined based on the anatomical characteristics (e.g., the type, size, location, property, structure, thickness, density, etc.) of the target and/or intervening tissues so as to achieve a peak intensity at the target. During the ultrasound procedure, the controller 108 may then drive the transducer elements 104 to emit ultrasound waves with the optimized frequency. Approaches to determining an optimal ultrasound transmission frequency are provided, for example, in U.S. patent application Ser. No. 16/233,744 (filed on Dec. 27, 2018), the content of which is incorporated herein by reference.

Accordingly, various embodiments of the present invention advantageously provide approaches to optimally determine the temporal profile parameters (e.g., the mode of operation, amplitude, frequency, and/or phase) associated with each transducer element 104 (or each group of the elements 104) during the ultrasound procedure; the profile parameters enable the transducer array to simultaneously generate a focal zone with desired focusing properties at the target region for effective treatment and measure high-quality acoustic signals from the microbubbles for the purposes of autofocusing, monitoring the microbubble activity and/or selecting optimal frequencies for the ultrasound procedure.

Figure 5A:
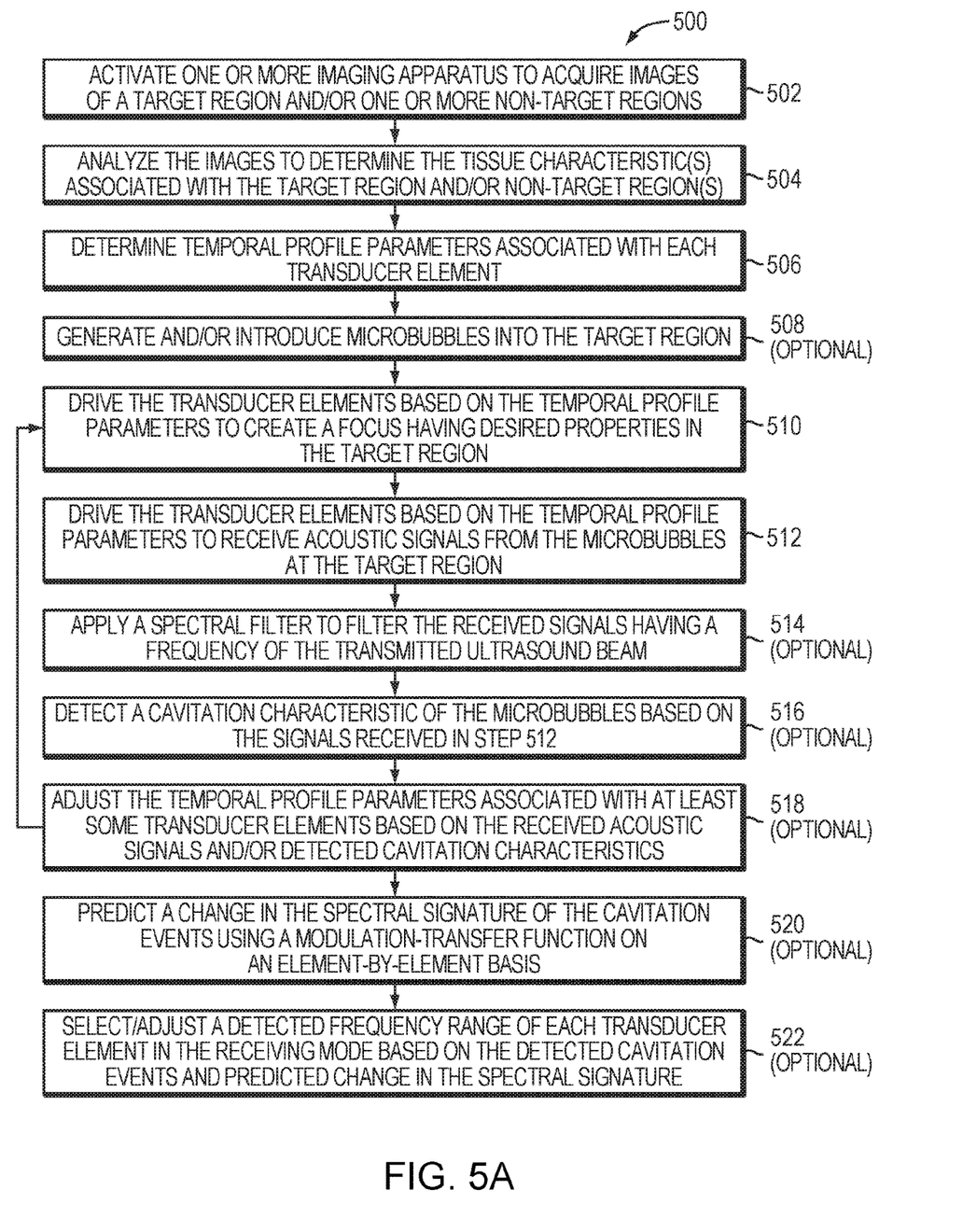
FIG. 5A is a flow chart illustrating an exemplary approach for driving the transducer elements to generate a high-quality focal zone at the target region and enable measurements of high-quality signals from the target region in accordance with various embodiments.

FIG. 5A is a flow chart illustrating an approach 500 for driving the transducer elements 104 to generate a high-quality focal zone at the target region 101 and enable measurements of high-quality signals from the target region in accordance herewith. In a first step 502, one or more imagers 112 are activated to obtain the images of a target region and/or one or more non-target regions (e.g., the region surrounding the target region and/or on the path zones located on the beam paths between at least some of the transducer elements and the target region). In a second step 504, the obtained images are analyzed to determine one or more tissue characteristics (e.g., the tissue type, location, size, thickness, density, structure, shape, vascularization, thermal time constant, etc.) associated with the target region and/or non-target region(s). In a third step 506, the temporal profile parameters (e.g., a mode of operation, an amplitude, a frequency and/or a phase) associated with each transducer element can be determined based at least in part on the determined tissue characteristic(s). Optionally, the microbubbles may be generated and/or introduced, directly or indirectly, into the target region (step 508). In a step 510, at least some of the transducer elements may be driven based on the determined temporal profile parameters to create a focus in the target region with desired properties. In addition, based at least in part on the profile parameters, at least some of the transducer elements may be driven based on the determined temporal profile parameters to receive acoustic signals from the microbubbles at the target region (step 512). The transducer elements driven to transmit acoustic waves to the target in step 510 may be the same as or different from the transducer elements driven to receive acoustic signals from the microbubbles in step 512. In some embodiments, one or more of the transducer elements are substantially simultaneously operated to transmit acoustic waves to the target and to receive acoustic signals from the microbubbles. For example, a time-division multiplexer may be implemented such that the substantially simultaneously operated transducer elements are operated during different time slices. In one embodiment, a spectral filter is optionally applied to filter the received signals having a frequency of the transmitted ultrasound beam (step 514).

In various embodiments, based at least in part on the signals received in step 512, a cavitation characteristic (e.g., a cavitation type and/or a cavitation location) of the microbubbles can be detected (step 516). Based on the received acoustic signals and/or detected cavitation characteristics, the temporal profile parameters (e.g., a mode of operation, an amplitude, a frequency and/or a phase) associated with at least some transducer elements can be adjusted to thereby improve the focus at the target region (step 518). Steps 510-518 may be iteratively performed until a focus having desired properties is created in the target region. In some embodiments, a change in the spectral signature of the cavitation events can be predicted using a modulation transfer function (i.e., the magnitude response of the system to sinusoids of different spatial frequencies) on an element-by-element basis (step 520). Based on the detected microbubble cavitation events and the predicted change in the spectral signature, the detected frequency range of each transducer element in the receiving mode can be selected or adjusted (e.g., using filters) so as to allow more sensitive measurement of the signals from the microbubbles (step 522).

Figure 5B:
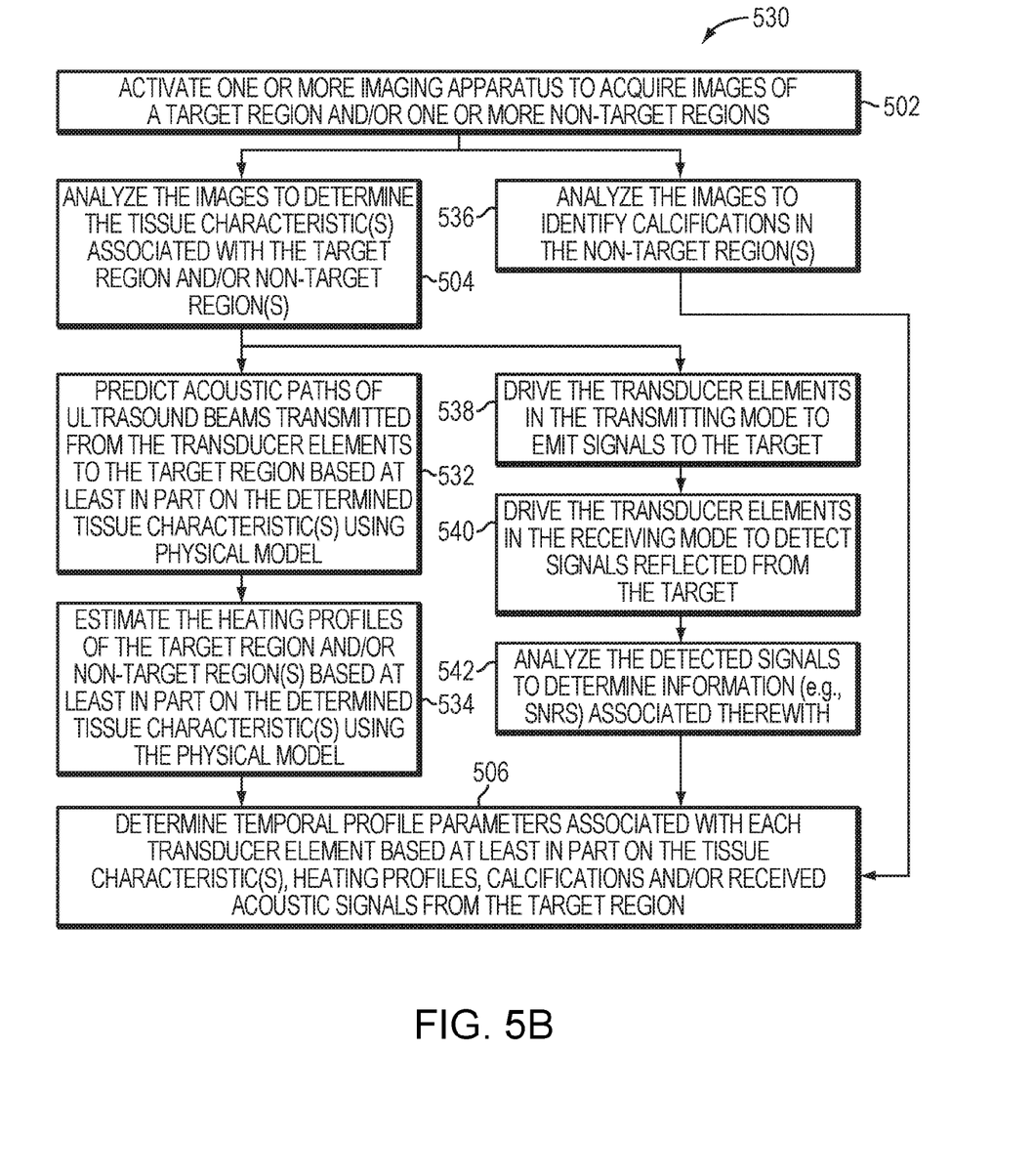
FIG. 5B is a flow chart illustrating an exemplary approach for determining temporal profile parameters associated with the transducer elements in accordance with various embodiments.

FIG. 5B is a flow chart illustrating an exemplary approach 530 for determining temporal profile parameters associated with the transducer elements in accordance herewith. In various embodiments, after the tissue characteristic(s) associated with the target region and/or non-target region(s) are determined, a physical model including a thermo-acoustic simulation may be implemented to predict acoustic paths of ultrasound beams transmitted from the transducer elements to the target region based at least in part on the determined tissue characteristic(s) (step 532). In addition, the physical model may estimate the heating profiles of the target region and/or non-target region(s) based at least in part on the determined tissue characteristic(s) (step 534). Additionally or alternatively, the images acquired in step 502 may be analyzed to identify calcifications in the non-target region(s) (step 536). In some embodiments, after the transducer elements are calibrated but prior to being activated for the ultrasound procedure, all (or at least some) transducer elements are operated in the transmitting mode to emit signals to the target (step 538). The transducer elements may be subsequently switched to the receiving mode to detect signals reflected from the target (step 540). The detected signals may be analyzed by the controller 108 to determine information (e.g., SNRs) associated therewith (step 542). In various embodiments, based on the tissue characteristic(s), heating profiles, calcifications and/or received acoustic signals from the target region, the temporal profile parameters associated with each transducer element may be determined (step 506).

In general, functionality for driving the transducer elements to generate a high-quality focal zone at the target region and enable measurements of high-quality signals from the target region as described above may be structured in one or more modules implemented in hardware, software, or a combination of both, whether integrated within a controller of the ultrasound system 100, an imager 112, and/or the administration system 126, or provided by a separate external controller or other computational entity or entities. Such functionality may include, for example, analyzing imaging data of the target and/or non-target regions acquired using an imager 112, determining a region of the target tissue and/or non-target tissue based on the imaging data, determining the anatomical/tissue characteristics (e.g., the tissue type, location, size, thickness, density, structure, shape, vascularization, thermal time constant, etc.) associated with the target/non-target tissue, analyzing the images to identify calcifications in the non-target region(s), using a physical model to predict acoustic paths of ultrasound beams transmitted from the transducer elements to the target region and estimate the heating profiles of the target region and/or non-target region(s), causing microbubbles to be generated and/or introduced in the target region, driving all (or at least some) transducer elements in the transmitting mode to emit signals to the target, driving all (or at least some) transducer elements in the receiving mode to detect signals reflected from the microbubbles at the target, analyzing the detected signals to determine information (e.g., SNRs) associated therewith, determining temporal profile parameters associated with each transducer element based at least in part on the tissue characteristic(s), heating profiles, calcifications and/or received acoustic signals from the target region, driving the transducer elements based on the temporal profile parameters to create a focus having targeted focusing properties in the target region, driving the transducer elements based on the temporal profile parameters to receive acoustic signals from the microbubbles at the target region, applying a spectral filter to filter the received signals having a frequency of the transmitted ultrasound beam, detecting a cavitation characteristic of the microbubbles based on the received signals, adjusting the temporal profile parameters associated with at least some transducer elements based on the received acoustic signals and/or detected cavitation characteristics, predicting a change in the spectral signature of the cavitation events using a modulation-transfer function on an element-by-element basis, and selecting/adjusting a detected frequency range of each transducer element in the receiving mode based on the detected cavitation events and predicted change in the spectral signature, as described above.

In addition, the ultrasound controller 108, the MR controller 148 and/or the controller associated with the administration system 126 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for generating an ultrasound focus at a target region and receiving signals therefrom, the system comprising:
   an ultrasound transducer comprising a plurality of transducer elements;
   an imaging system for obtaining a plurality of images of the target region and one or more path zones located on beam paths between at least some of the transducer elements and the target region; and
   a controller, operably coupled to the ultrasound transducer and the imaging system, configured to:
   (a) determine at least one tissue anatomical characteristic associated with a non-target region in the one or more path zones between the at least some of the transducer elements and the target region based on the obtained images, wherein the at least one anatomical characteristic includes a structure, a thickness, a density, or a heating profile of the non-target region;
   (b) determine, for each of the transducer elements, a mode of operation comprising at least one of a transmitting mode or a receiving mode based at least in part on the at least one anatomical characteristic, wherein a non-target region structure, thickness, density, or heating profile associated with transducer elements determined to be in the transmitting mode is different from a non-target region structure, thickness, density, or heating profile associated with transducer elements determined to be in the receiving mode;
   (c) operate at least first ones of the transducer elements determined to be in the transmitting mode to collectively transmit an ultrasound beam to the target region so as to create a focus thereon; and
   (d) operate at least second ones of the transducer elements determined to be in the receiving mode to receive acoustic signals from the target region and, in response thereto, adjust operation of the at least first ones of the transducer elements to thereby alter the focus at the target region.

2. The system of claim 1, wherein:
   step (b) further comprises determining a plurality of profile parameters associated with each of the transducer elements based at least in part on the at least one anatomical characteristic, wherein the profile parameters further comprise at least one of an amplitude, a frequency or a phase associated with each of the transducer elements.

3. The system of claim 1, further comprising an administration device for introducing microbubbles into the target region, wherein the received signals are reflections from the microbubbles.

4. The system of claim 1, further comprising an administration device for introducing a seed microbubble, wherein the controller is further configured to cause generation of a cloud of microbubbles at the target region using the seed microbubble and the ultrasound transducer, wherein the received signals are reflections from the microbubbles.

5. The system of claim 1, wherein the controller is further configured to cause generation of microbubbles in the target region using the ultrasound transducer, wherein the received signals are reflections from the microbubbles.

6. The system of claim 5, wherein the controller is further configured to detect a cavitation characteristic of the microbubbles based at least in part on the received signals.

7. The system of claim 6, wherein the cavitation characteristic comprises at least one of a cavitation type or a cavitation location.

8. The system of claim 5, wherein the controller is further configured to:
   determine the mode of operation for each of the transducer elements based at least in part on the received signals; and operate the first and second ones of the transducer elements based on the mode of operation for each of the transducer elements.

9. The system of claim 1, wherein the imaging system is configured to obtain a second plurality of images of at least one of a first tissue region surrounding the target region or a second tissue region on one of the path zones, and the controller is further configured to determine at least a second anatomical characteristic associated with the first tissue region and/or the second tissue region based on the obtained second plurality of images.

10. The system of claim 9, wherein the controller is further configured to:
determine the mode of operation for each of the transducer elements based at least in part on the second anatomical characteristic; and
adjust operation of the transducer elements based on the respective determined mode of operation.

11. The system of claim 9, wherein the controller is further configured to:
predict acoustic paths of ultrasound beams transmitted from the first ones of the transducer elements; and
estimate heating profiles of the first and second regions based at least in part on the second anatomical characteristic.

12. The system of claim 11, wherein the acoustic path prediction and heating profile estimation is performed using a physical model comprising a thermo-acoustic simulation.

13. The system of claim 1, wherein at least some of the first ones of the transducer elements are different from at least some of the second ones of the transducer elements.

14. The system of claim 1, wherein at least some of the first ones of the transducer elements are the same as at least some of the second ones of the transducer elements.

15. The system of claim 14, wherein the controller is further configured to substantially simultaneously operate the first ones of the transducer elements that are the same as the second ones of the transducer elements.

16. The system of claim 15, further comprising a spectral filter for filtering the received signals having a frequency of the transmitted ultrasound beam.

17. The system of claim 14, further comprising a time-division multiplexer, wherein the first ones of the transducer elements and the second ones of the transducer elements are operated during different time slices.

18. The system of claim 17, wherein a first time interval of the time slices associated with operation of the first ones of the transducer elements is the same as a second time interval of the time slices associated with operation of the second ones of the transducer elements.

19. The system of claim 17, wherein a first time interval of the time slices associated with operation of the first ones of the transducer elements is different from a second time interval of the time slices associated with operation of the second ones of the transducer elements.

20. The system of claim 1, wherein the controller is further configured to determine a frequency range of the received acoustic signals.

21. The system of claim 20, further comprising a spectral filter for filtering the received signals having frequencies outside the frequency range.

22. The system of claim 21, wherein the controller is further configured to determine the frequency range based on a second anatomical characteristic associated with an intervening tissue located in at least one of the path zones.

23. The system of claim 1, wherein the controller is further configured to determine an optimal transmission frequency associated with the first ones of the transducer elements for maximizing an acoustic intensity at the target region.

24. The system of claim 23, wherein the controller is further configured to determine the optimal transmission frequency based at least in part on the anatomical characteristic of the target region and a second anatomical characteristic associated with an intervening tissue located in at least one of the path zones.

25. The system of claim 1, wherein the controller is configured to determine the mode of operation for each transducer element based at least in part on one or more anatomical characteristics of a non-target region in the beam path between the transducer element and the target region.

26. The system of claim 25, wherein the one or more anatomical characteristics comprise a structure, a thickness, or a density of the non-target region.

27. The system of claim 26, wherein the thickness of a first non-target region associated with a first transducer element of the plurality of transducer elements associated with a transmitting mode is thinner than the thickness of a second non-target region associated with a second transducer element of the plurality of transducer elements associated with a receiving mode.

28. The system of claim 27, wherein the first non-target region and the second non-target region are regions of a skull.

* * * * *